United States Patent [19]

Villette

[11] Patent Number: 4,787,893
[45] Date of Patent: Nov. 29, 1988

[54] INSTRUMENT FOR INJECTING BIOCOMPATIBLE PRODUCTS THROUGH BONE TISSUE

[76] Inventor: Alain Villette, Les Vannes, FR-79700 St Pierre des Echaubrognes, France

[21] Appl. No.: 878,134

[22] Filed: Jun. 25, 1986

[51] Int. Cl.⁴ .............................................. A61M 5/00
[52] U.S. Cl. .................................. 604/188; 604/154; 604/131; 433/118
[58] Field of Search ............... 604/154, 155, 188, 67, 604/156, 92 UD, 131; 222/390; 128/DIG. 1, 655; 433/118

[56] References Cited

U.S. PATENT DOCUMENTS

| 1,523,068 | 1/1925 | Hein | 604/188 |
| 2,773,500 | 12/1956 | Young | 604/188 |
| 3,811,442 | 5/1974 | Maroth | 604/188 |
| 4,381,777 | 5/1983 | Garnier | 604/188 |
| 4,620,848 | 11/1986 | Sutherland et al. | 604/154 |

FOREIGN PATENT DOCUMENTS 2077599 12/1981 United Kingdom ............... 604/154

Primary Examiner—C. Fred Rosenbaum
Assistant Examiner—Colleen M. Reilly
Attorney, Agent, or Firm—Thomas A. O'Rourke

[57] ABSTRACT

An instrument by which a biocompatible liquid or semi-liquid formulation is injected through bone tissue. The device has a needle (16) removably mounted at the end of a carpule (13). The carpule has a moving base wall, means (4, 8, 9, 12) for rotating the carpule and the needle, and a motor (5) for applying a force to the moving base wall of the carpule. The motor (5) applies the force to the moving base wall via a rack (17) which bears against the moving base wall of the carpule.

12 Claims, 3 Drawing Sheets

INSTRUMENT FOR INJECTING BIOCOMPATIBLE PRODUCTS THROUGH BONE TISSUE

The present invention relates to an instrument for injecting through bone tissue, and is intended in particular for performing intramedullary injections of biocompatible products in liquid or semi-liquid form.

BACKGROUND OF THE INVENTION

Injections are made through bone tissue for diagnostic and for therapeutic purposes, and in particular for obtaining local anesthesia of the teeth on which a dentist is about to operate.

In dental anesthesia, the conventional solution consists in using a conventional syringe to inject a predetermined quantity of liquid anesthetic into the patient's gum at a certain distance from the toot to be treated (block, conduction, and para-apical anesthesia). As it diffuses from the point of injection, the anesthetic anesthetizes the surrounding region which includes the tooth to be treated. This solution suffers from the following drawbacks: the injection is performed blind; there is a period of latency between the injection and the tooth to be treated becoming anesthetized; more anesthetic is used than would be necessary for anesthetizing the tooth only; the patient is left with a disagreeable sensation in the mouth which lasts for a long time after the dentist has finished working on the tooth; etc.

Proposals have already been made to remedy these drawbacks by using an intramedullary anesthetic which is injected into the porous (ethmoid) bone of the upper or lower jaw in the immediate vicinity of the tooth to be treated. However, in this case it is necessary to pass through the hard shell or osseous cortex of the bone before injecting the anesthetic. French published patent specification No. 2 457 105 describes a syringe suitable for performing this operation. The syringe described in that French patent rotates the needle to enable it to pass through the cortex, with the injection per se then being performed along the hollow needle by drawing a moving trigger towards a fixed rest, with the moving trigger operating a piston which displaces a carpule type cartridge or store of anesthetic. The needle and the carpule are rotated either by a mechanical drive of the type available next to a dentists' chair and generally used for driving a dental drill, or else by means of a small motor disposed inside the syringe and connected to a suitable supply of electricity.

The method and the apparatus described in the above-mentioned patent specification have considerably improved dental surgery in that, relative to conventional anesthesia, they provide: greater freedom in selecting the site at which to perform the injection; greater latitude in the angle of approach of the needle; and a relatively small quantity of anesthetic is actually injected into the porous bone.

However, this syringe suffers from drawbacks. In particular, there is a danger of the channel along the hollow needle becoming obstructed, for example by a mixture of bone dust and blood as it passes through the cortex. This may happen if the speed of rotation is too low, or if the force with which the needle is pressed against the bone is too high. When the channel along the needle has become obstructed, the pressure exerted on the anesthetic must be increased. This has two unfortunate consequences: the extra effort required of the practitioner causes the needle to tremble and thus spoils the accuracy with which the needle is located and also spoils the evenness of the rate at which anesthetic is injected. In particular, the sudden rush of liquid under pressure into the porous bone which occurs immediately after the obstruction has been ejected is particularly painful for the patient.

Preferred embodiments of the present invention mitigate these drawbacks by automating operation of the instrument in such a manner as to ensure that the anesthetic (or more generally any liquid to be injected into a bone) is injected evenly. Preferably, the electrical power supply to the instrument is completely independent from the dentists' chair so as to avoid the need for any connecting wire which could hinder the manipulations performed by the dentist.

Further, and more generally, all prior known syringes have had to imitate the cylindrical shape of a conventional syringe. However, this shape is poorly adapted to the work of injecting through bone since the syringe should be capable of being firmly gripped in the hand in order to ensure that positional accuracy is maintained throughout the injection operation. Preferred embodiments of the present invention also improve the accuracy with which the instrument can be manipulated by providing an apparatus having a good hand hold.

SUMMARY OF THE INVENTION

According to the present invention, an injection instrument, in particular for injecting through bone tissue, comprises a needle removably mounted on one end of a carpule, means for rotating the carpule, and means for applying pressure to a moving base of the carpule, and includes the improvement whereby the means for causing the carpule to rotate and for building up a pressure therein are constituted by two motors mounted within the body of the instrument and respectively connected to rotate the carpule and to drive a piston whose leading end bears against the moving base of the carpule and whose advance is regulated by a speed reduction gear.

Once the cortex has been perforated, even and continuous injection can automatically be obtained by setting suitable parameters for the speed of rotation of the piston drive motor and for the speed reduction gear.

The instrument is preferably provided with electronic safety means for stopping injection by acting on the piston drive motor in the event that the needle should become totally obstructed or that its tip should be located in non-porous bone.

The body of the instrument is preferably in the form of a pistol-grip or stock including both the motors and a rechargeable battery set.

The motors are preferably powered from a rechargeable dry battery set. This makes the instrument completely independent from the dentists' chair and it may be capable of operating for a period of about two days without being recharged.

BRIEF DESCRIPTION OF THE DRAWINGS

An embodiment of the invention is described by way of example with reference to the accompanying drawings, in which.

MORE DETAILED DESCRIPTION

In the example described below the injector instrument is intended for injecting anesthetic through bone tissue, but it should be understood that its theory of operation is applicable *mutatis mutandis* to injecting any biocompatible liquid or semi-liquid substance such as a gell through bone tissue.

Figure 1:
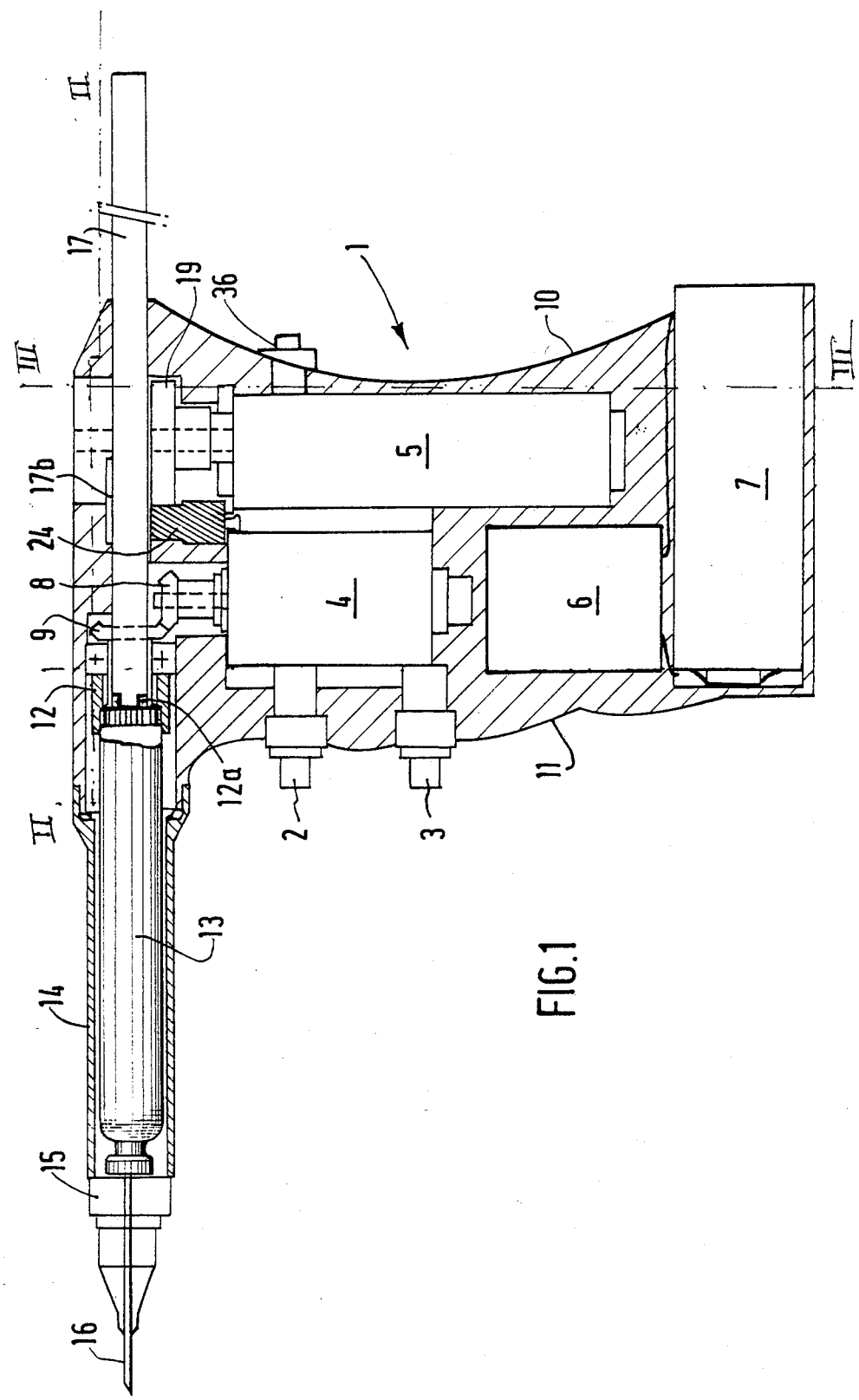
FIG. 1 is vertical section through an injector instrument in accordance with the invention.
Figure 3:
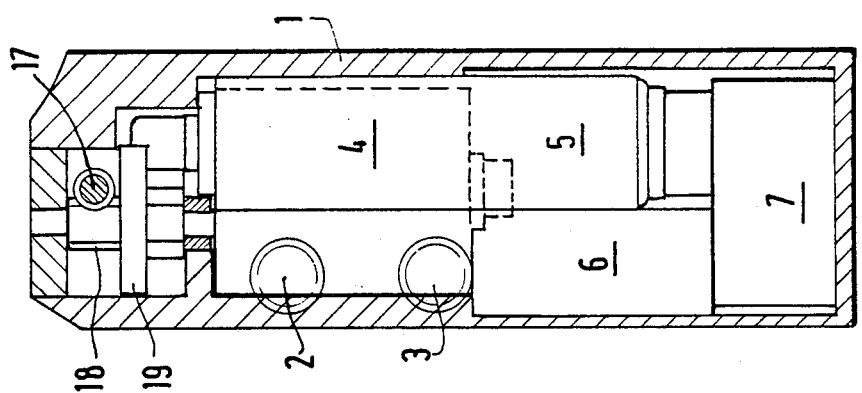
FIG. 3 is a vertical section on a line III—III through the rear of the instrument shown in FIG. 1.
Figure 2:
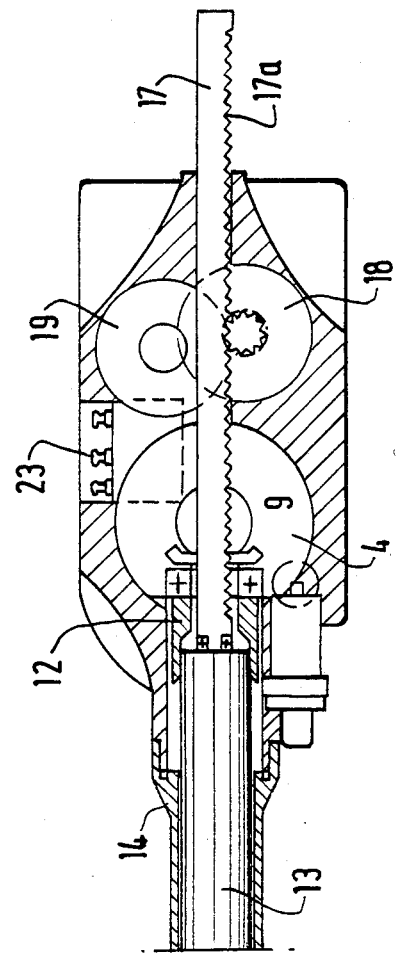
FIG. 2 is a horizontal section on a line II—II through the top of the instrument shown in FIG. 1.

In FIGS. 1, 2 and 3, the body 1 of an injector instrument is generally in the shape of a pistol-grip or stock, with a concave rear portion 10 and a convex front portion 11 shaped for receiving a dentist's fingers when the palm of the hand is pressed against the concave portion 10. The top of the rear concave surface 10 has a general ON/OFF switch 36 which controls the electronic circuit 6 for controlling the motors. In a variant embodiment, the switch 36 could be used for causing the piston to move rearwardly, e.g. when injecting only a portion of the contents of the carpule. Two other switches 2 and 3 are located on the front of the stock and act respectively to switch on a motor 4 for rotating the carpule and to switch on a motor 5 for injecting its contents. Movement of the motors is under the control of an electronic control circuit 6 which is described in greater detail below and the power supply for the motors passes through the control circuit 6 from a rechargeable battery set 7 which delivers a suitable DC voltage, e.g. 8 volts. The injector is advantageously placed, after use, on a support for automatically recharging the batteries.

The output shaft of the motor 4 has a gearwheel 8 meshing with a gearwheel 9 fixed to a sleeve 12 which is a friction fit on the rear portion of the carpule or cartridge 13. The sleeve 12 is glued to a tube which is fixed to the gearwheel 9 and the assembly is held in position by a bearing suitable for allowing rotation thereof. The carpule 13 is capable of rotating inside a housing 14 whose front end 15 constitutes a front bearing for guiding the needle 16. The moving base of the carpule 13 is in contact with a piston 17 having a rack with teeth 17a that mesh with a gearwheel 18 (see FIG. 2) which is driven via a speed reducing gear by a gearwheel 19 fixed to the output shaft of the motor 5. The front end of the piston 17 makes contact with the base of the carpule via a ball abutment 12a suitable for transmitting pressure longitudinally to the piston 17 while the carpule 13 is caused to rotate.

The injector instrument operates as follows: initially the needle is placed with its large chamfered front end portion flat against the gum, and a short jab to the switch 3 causes a small quantity of anesthetic to be released, thereby instantaneously anesthetizing the gum mucous membrane. The practitioner simultaneously guides the needle so that it penetrates through the mucous membrane. The structure of the instrument makes it possible for the practitioner to concentrate on the operation of guiding the needle, whereas with a conventional syringe the practitioner would be obliged to monitor both movements simultaneously. The needle 16 is then caused to rotate by pressing on the switch 2. The needle penetrates through the cortex. The speed and the perforation torque provided by this injector instrument are greater than those obtained by the instrument described in the above-mentioned specification, and as a result the present instrument generates very little noise.

Once the needle has passed through the cortex, injection per se may begin by operating the switch 3 which causes the motor 5 to rotate and thereby causes the piston 17 to move forwardly, thus expelling the liquid contained in the carpule 13 at an average pressure of 65 bars per $cm^2$, for example, which is a much higher pressure than can be obtained by hand. Also, the speed of injection is predetermined to be less than the pain threshold and to be constant regardless of the tissue being injected, thus avoiding jolting. When the carpule is empty, the piston returns automatically to its starting position. The forwards and backwards movement of the piston is automated by means of end-of-stroke contacts for detecting the front (23, see FIG. 2) and the rear (24, see FIG. 1) end positions, with the end-of-stroke contacts co-operating with a peg 17b provided on the piston.

Figure 4:
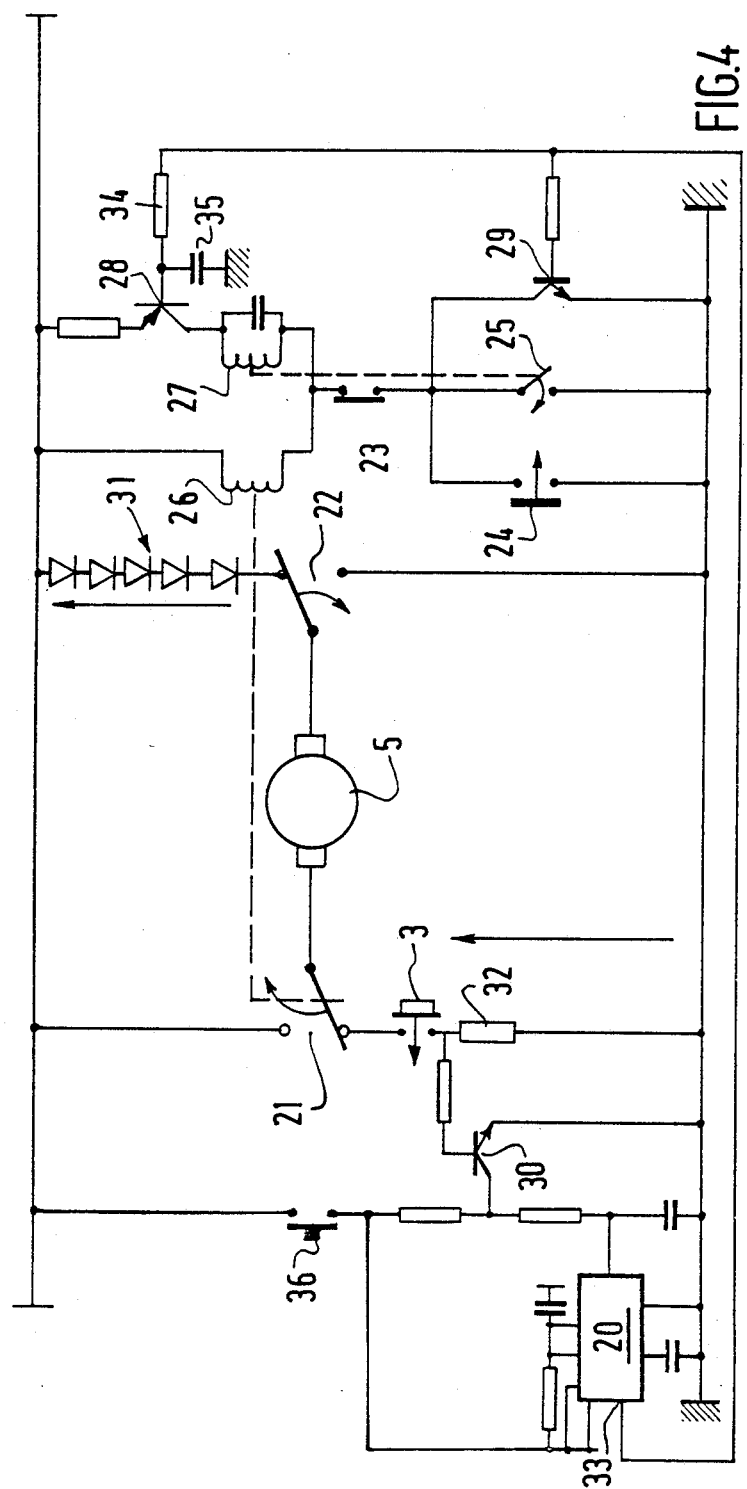
FIGS. 4 and 5 are diagrams of the control circuits for the motors.

FIG. 4 is an electronic circuit diagram of the control circuit for controlling translation of the piston rod 17 having the rack which co-operates with the gearwheel 18. This diagram shows the drive motor 5, its control pushbutton 3, and the overall ON/OFF switch 36 for avoiding any current drain when the instrument is not in use. The control circuit per se comprises a monostable integrated circuit (IC) 20, e.g. of the NE 555 type and two reversing switches 21 and 22 directly connected to the terminals of the motor 5. The switches 21 and 22 are controlled by an electromagnet winding 26. A switch 25 controlled by a relay 27 serves to provide automatic holding for the electromagnet. The circuit also includes the rear end-of-stroke contact 23, the front end-of-stroke contact 24, a switch 25, and three control transistors 28, 29 and 30. In the circuit diagram, the various components are shown in the positions which they occupy when the rack is moving forwards. In this position, the rear end-of-stroke contact 23 is open and the motor is powered from the voltage source at 8 volts, for example, via a divider bridge constituted by a series of diodes 31 and a resistance 32. The motor is thus powered at reduced voltage enabling the piston 17 to advance slowly, and piston advance is directly under the control of the dentist operating the switch 3. If the needle becomes blocked while the piston 17 is advancing, as described above, the motor encounters greater resistance than usual. As a result, extra current passes through the resistance 32 and this extra current is detected by the monostable IC 20 by means of a transistor 30 whose base voltage is altered by the extra current. When the increase in motor current exceeds a limit value stored by the circuit 20 and equal, for example, to 0.575 milliamps, the needle is deemed to be obstructed and the integrated circuit 20 is triggered thereby applying a control signal on its terminal 33. This signal is applied, in turn, to the bases of transistors 28 and 29. This alters the bias of said transistors and increases their collector current, thereby changing the current passing though the electromagnet 26 and switching over switches 21 and 22 causing the motor to rotate in the opposite direction, thereby moving the rack rearwardly. As can be clearly seen from the circuit diagram, the motor is directly connected between the voltage source and ground at this moment. As a result it operates at maximum speed and moves backwards until the rear end-of-stroke contact 23 closes. After a predetermined period of time, for example after 1 to 2 seconds, the monostable IC 20 ceases to apply its control signal, and when it returns to its rest position, the transistor 29 is turned off, and after a delay determined by an RC circuit constituted by a resistance 34 and capacitance 35, the transistor 28 saturates again, thereby returning the reversing switches 21 and 22 to their initial positions, from which the piston drive motor 5 is once again under the control of the switch 3, as before.

When the piston 17 arrives at its front end position, the front end-of-stroke contact 24 closes without the dentist intervening, thereby changing the current flowing through the winding 26 and causing the reversing switches 21 and 22 to change state. The rack reverses at maximum speed as when the needle is blocked and continues moving backwards until it reaches its extreme rear position, in which it closes the rear end-of-stroke contact 23.

Figure 5:
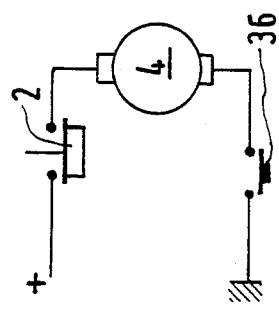

FIG. 5 is a circuit diagram of the power supply to the motor 4 used for rotating the needle. This motor is connected between the positive terminal of the storage battery 7 and ground, and is directly controlled by the switch 2.

In another embodiment, the needle used has a side opening in the vicinity chamfer at the leading end in addition to its above-mentioned axial opening, and the side opening serves to facilitate penetration into tissue. The side orifice may extend from a central bore of the needle in a rearwards direction. If the practitioner acts too roughly or too quickly, the central channel is almost always blocked. In some particularly compact cortex structures, it is practically impossible for the needle to pass through. In this case, the above-described control circuit operates by causing the needle to be withdrawn rapidly and the anesthetic must be administered conventionally. However, if the cortex is indeed passed through, and even if the axial channel is obstructed, injection can still take place by the liquid flowing out through the side opening.

For a needle having a diameter of 40/100-ths of a centimeter, the central opening has a diameter of 12/100-ths of a centimeter. Laser drilling techniques can be used to make a rearwardly facing side opening or window through such a needle at an angle to the needle axis and having a diameter of 2/100ths to 3/100-ths of a centimeter. This disposition makes it possible to inject anesthetic even when the central channel is obstructed, and without having to withdraw the needle from the cortex, then changing the needle and re-inserting it into the initial hole drilled through the cortex. It thus becomes possible to perform an injection through bone tissue as easily as an injection into soft tissue.

Naturally, numerous variations of the invention are possible without going beyond the scope of the accompanying claims. In particular various means may be replaced by technically equivalent means.

I claim:

1. An instrument for injecting a biocompatible liquid or semi-liquid formulation through bone tissue, comprising an hollow body and means at its upper part to bear a carpule containing the formulation, a needle removably mounted at one end or the carpule, the other end being closed by a moving base wall wherein said hollow body includes an electronic circuit and two motors, the first motor rotating said carpule via a first gear train, the second motor driving a piston having a front portion bearing against said moving wall of the carpule, said piston being driven via a second gear train, said motors being controlled by switches connected to said electronic circuit, the rear portion of the carpule being in a friction fit with a sleeve fixed to a gear wheel, said rear portion passing through the sleeve.

2. An injector instrument according to claim 1, wherein the teeth of said rack mesh with the teeth of said second gear driven by said second motor via speed-reducing gear.

3. An injector instrument according to claim 1, wherein said electronic circuit includes means for detecting an increase in the current flowing through said second motor corresponding to the needle being obstructed.

4. An injector instrument according to claim 2 or 3, wherein said electronic circuit includes switches for reversing the direction of power supply to said second motor.

5. An injector instrument according to claim 1, wherein said instrument body is shaped like a pistol-grip, having a palm-receiving rear face and a finger-receiving front face, said first and second motors and said electricity power supply being contained in said body.

6. An instrument for injecting a biocompatible liquid or semi-liquid formulation through bone tissue comprising a needle removably mounted on one end of a carpule having a moving base wall, a means for rotating the carpule and the needle and means for applying pressure to a moving base of the carpule via a rack having a front portion bearing against said moving base wall of the carpule, the instrument including the improvement whereby the means for rotating the carpule and the means for applying a force to its base are constituted by first and second motors connected to an electronic circuit and included in the body of the instrument, said first motor rotating said carpule via a first gear train, said second motor driving said rack via a second gear train, said motors being controlled by switches connected to an electricity supply via said electronic circuit said instrument including a means for adjusting the speed of rotation of said first motor and the speed of the reduction gear to provide even and continuous injection of the biocompatible liquid or semi-liquid formulation.

7. An instrument for injecting a biocompatible liquid or semi-liquid formulation through bone tissue comprising a body having a pistol grip, said body having a carpule including a removable needle therein said body also including first and second motors and an electronic circuit for controlling said motors, said first motor adapted to rotate said carpule by means of first and second gears, said second gear being connected to a rotatable sleeve which is friction fit on the rear portion of the carpule said carpule being rotatable inside a housing in said body, said housing having a guide means for guiding the needle in said carpule during injection, said second motor providing the means for injecting the contents of the carpule and having a speed reducing gear connected by means rack assembly to a piston, said assembly including a means for transmitting pressure longitudinally to said piston while said carpule is caused to rotate.

8. An injector instrument according to claim 1 having an electronic safety means for ceasing injection of the biocompatible liquid or semi-liquid formulation upon obstruction of the needle.

9. An injector instrument according to claim 1 wherein biocompatible liquid or semi-liquid formulation is injected at pressure of about 65 bars per $cm^2$.

10. An injector according to claim 1 wherein said hollow body includes a battery connected to said electric circuit.

11. An injector instrument for injecting a biocompatible liquid or semi-liquid formulation through bone tissue, comprising a hollow body and means at its upper part to bear a carpule containing the formulation, a needle removably mounted at one end of the carpule, the other end being closed by a moving base wall wherein said hollow body includes an electric circuit and two motors, the first motor rotating said carpule via a first train and said second motor driving a piston via a second gear train said motors being controlled by switches connected to said electronic circuit, said electronic circuit for controlling the piston comprising a monostable integrated circuit and two reversing switches directly connected to the terminals of said second motor said switches being controlled by an electromagnetic winding, said electromagnetic winding having a contact controlled by a relay, said circuit also including a rear end of stroke contact, a front end of stroke contact, a switch and first, second and third control transistors whereby said first control transistor detects an electric current in said monostable integrated circuit and said second and third transistors signalling to said electromagnet resistance to the needle during injection.

12. An injector instrument according to claim 8 wherein said needle includes an axially-directed end orifice and a side orifice.

* * * * *